(12) United States Patent
Youn et al.

(10) Patent No.: US 10,545,114 B2
(45) Date of Patent: Jan. 28, 2020

(54) CHEMICAL SENSOR AND A METHOD FOR MANUFACTURING THE SAME

(71) Applicant: Electronics and Telecommunications Research Institute, Daejeon (KR)

(72) Inventors: Doo Hyeb Youn, Daejeon (KR); Sun Jin Yun, Daejeon (KR); Changbong Yeon, Namyangju-si (KR); Young-Jun Yu, Daejeon (KR); HongKyw Choi, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 133 days.

(21) Appl. No.: 15/947,213

(22) Filed: Apr. 6, 2018

(65) Prior Publication Data
US 2018/0372677 A1 Dec. 27, 2018

(30) Foreign Application Priority Data

Jun. 21, 2017 (KR) .................. 10-2017-0078727
Sep. 25, 2017 (KR) .................. 10-2017-0123733
Dec. 18, 2017 (KR) .................. 10-2017-0174375

(51) Int. Cl.
*G01N 27/414* (2006.01)
*G01N 31/10* (2006.01)
(Continued)

(52) U.S. Cl.
CPC ....... *G01N 27/4141* (2013.01); *G01N 27/127* (2013.01); *G01N 27/4146* (2013.01); *G01N 31/10* (2013.01); *D01D 5/0038* (2013.01)

(58) Field of Classification Search
CPC .... G01N 27/12; G01N 27/125; G01N 27/127; G01N 27/403; G01N 27/4141; G01N 27/4143; G01N 27/4146; D01D 5/0038
(Continued)

(56) References Cited

U.S. PATENT DOCUMENTS 5,876,578 A  3/1999 Yamauchi et al.
2008/0150556 A1* 6/2008 Han .................. B82Y 15/00
324/693

(Continued)

FOREIGN PATENT DOCUMENTS

KR  10-2010-0138089 A  12/2010
KR    10-1673112 B1  11/2016

OTHER PUBLICATIONS

Sun-Woo Choi et al., "NO$_2$-sensing performance of SnO$_2$ microrods by functionalization of Ag nanoparticles", Journal of Materials Chemistry C, vol. 01, pp. 2834-2841, Feb. 21, 2013.
(Continued)

*Primary Examiner* — Benjamin R Schmitt
(74) *Attorney, Agent, or Firm* — Rabin & Berdo, P.C.

(57) ABSTRACT

Provided is a chemical sensor which includes an alignment frame that has an opening that passes through the inside of the alignment frame and includes first and second side portions that face each other with the opening therebetween and insulation portions disposed between the first and second side portions, a plurality of sensing fibers disposed in two-dimensions across the opening of the alignment frame so as to connect the first side portion and the second side portion, and a source pattern and a drain pattern connected to the first side portion and the second side portion of the alignment frame, respectively.

13 Claims, 8 Drawing Sheets

(51) Int. Cl.
*G01N 27/12* (2006.01)
*D01D 5/00* (2006.01)

(58) Field of Classification Search
USPC .................................. 73/23.2, 31.05, 31.06
See application file for complete search history.

(56) References Cited

U.S. PATENT DOCUMENTS

| | | | |
|---|---|---|---|
| 2009/0233374 A1* | 9/2009 | Zang | G01N 21/6428 |
| | | | 436/106 |
| 2012/0108465 A1* | 5/2012 | Duoss | B82Y 15/00 |
| | | | 506/12 |
| 2016/0077069 A1 | 3/2016 | Kim et al. | |
| 2017/0045473 A1 | 2/2017 | Yu et al. | |
| 2017/0171965 A1 | 6/2017 | Youn et al. | |

OTHER PUBLICATIONS

Dae-Jin Yang et al., "Ultrasensitive and Highly Selective Gas Sensors Based on Electrospun $SnO_2$ Nanofibers Modified by Pd Loading", Advanced Functional Materials, vol. 20, pp. 4258-4264, Sep. 7, 2010.

* cited by examiner

FIG. 9

CHEMICAL SENSOR AND A METHOD FOR MANUFACTURING THE SAME

CROSS-REFERENCE TO RELATED APPLICATIONS

This U.S. non-provisional patent application claims priority under 35 U.S.C. § 119 of Korean Patent Application Nos. 10-2017-0078727, filed on Jun. 21, 2017, 10-2017-0123733, filed on Sep. 25, 2017, and 10-2017-0174375, filed on Dec. 18, 2017, the entire contents of which are hereby incorporated by reference.

BACKGROUND

The present disclosure herein relates to a chemical sensor and a method for manufacturing the same, and more particularly, to a fiber type gas sensor and a method for manufacturing the same.

As the number of application fields using gas increases in addition to a case where gas is used as a traditional energy source, chemical sensors are being widely used. The chemical sensor is a device in which a detection material chemically interacts with a chemical substance to be detected on a surface thereof, and in this case, the device uses variation of electrical resistivity generated on the surface of the detection material. The typical chemical sensor has been used to detect toxic gas and explosive gas, but in recent years, many technologies for detecting gas and using the same are being developed in various fields such as health care, environmental pollution surveillance, industrial safety, home appliances and smart homes, food and agriculture, and national defense and terror. In various fields, many detection technologies have been suggested to sensitively and accurately detect a sample that is a material to be analyzed, which is included in a sample, and the currently commercialized chemical sensor uses an optical type, an electro-chemical type, a semiconductor type, a contact combustion type, a surface acoustic wave type, and the like.

Recently, various kinds of metal oxide semiconductors are manufactured as shapes of one-dimensional structure such as a fiber, a rod, a tube, or a ribbon, and the researches applying the above the structures are actively conducted. The material with the one-dimensional structure has physical characteristics or chemical properties which are different from or superior than a bulk material or a thin film material. The one dimensional structure material has a very large surface area with respect to its volume, and thus has advantageous characteristics in detecting various kinds of chemical species, and accordingly, the application of this material to nano chemical sensor is being attempted.

SUMMARY

The present disclosure provides a chemical sensor with high sensing sensitivity and a method for manufacturing the same.

The present disclosure also provides a chemical sensor capable of selectively detecting a plurality of target materials, and a method for manufacturing the same.

The purpose of the present disclosure is not limited to the aforesaid, but other purposes not described herein will be clearly understood by those skilled in the art from descriptions below.

An embodiment of the inventive concept provides a chemical sensor including: an alignment frame having an opening that passes through the inside of the alignment frame, the alignment frame including first and second side portions that face each other with the opening therebetween and insulation portions disposed between the first and second side portions; a plurality of sensing fibers disposed in two-dimensions across the opening of the alignment frame so as to connect the first side portion and the second side portion; and a source pattern and a drain pattern connected to the first side portion and the second side portion of the alignment frame, respectively.

In an embodiment, the sensing fibers may extend from a top surface of the first side portion to a top surface of the second side portion.

In an embodiment, the first side portion and the second side portion of the alignment frame may have bar shapes that are parallel in one direction. The sensing fiber may extend so as to cross the first direction.

In an embodiment, both ends of the first side portion may be connected to both ends of the second side portion through the insulation portions of the alignment frame, respectively.

In an embodiment, the alignment frame may have a plane with a rectangular ring shape.

In an embodiment, each of the first side portion and the second side portion may be an electric conductor.

In an embodiment, the sensing fibers may include at least one of $MoSe_2$, $WSe_2$, $MoS_2$, $WS_2$, $SnS_2$, $TeS_2$, $MoTe_2$, $WTe_2$, or black phosphorus.

In an embodiment, metal oxide particles disposed on outer surfaces of the sensing fibers may be further included.

In an embodiment of the inventive concept, a chemical sensor includes a plurality of sensor parts; and a substrate including a source pattern and a drain pattern that are electrically connected to the sensor parts. Each of the sensor parts may include: a first side portion that is conductive, and connected to the source pattern; a second side portion that is conductive, and connected to the drain pattern and spaced apart from the first side portion; insulation portions that connect both ends of the first side portion and both ends of the second side portion, respectively; and a sensing fiber that is disposed between the insulation portions to connect the first side portion and the second side portion. A sensing fiber in one of the sensor parts may detect a target material different from that of a sensing fiber in another one of the sensor parts.

In an embodiment, each of the source pattern and the drain pattern may extend in a first direction. The sensor parts may be horizontally spaced apart from each other in the first direction.

In an embodiment, the sensor parts may be vertically stacked. A first side portion in one of the sensor parts may overlap and contact a first side portion of a sensing fiber in another one of the sensor parts. A second side portion in one of the sensor parts may overlap and contact a second side portion of a sensing fiber in another one of the sensor parts.

In an embodiment of the inventive concept, a method for manufacturing a chemical sensor includes: forming a sensor part; and transferring the sensor part onto a substrate so as to be connected to a source pattern and a drain pattern of the substrate. The forming of the sensor part may include: providing an alignment frame, which has an opening, on a dummy substrate; forming a sensing fiber across the opening of the alignment frame; and separating the alignment frame from the dummy substrate.

In an embodiment, the alignment frame may include: first and second side portions that face each other with the opening therebetween and are insulated from each other; and insulation portions that connect both ends of the first side portion and both ends of the second side portion, respectively. The sensing fiber may connect the first side portion and the second side portion.

In an embodiment, the sensing fiber may be formed through an electro-spinning method.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Preferred embodiments of the inventive concept will be described with reference to the accompanying drawings so as to sufficiently understand constitutions and effects of embodiments of the inventive concept. The present disclosure may, however, be embodied in different forms with various changes and should not be construed as limited to the embodiments set forth herein. Rather, these embodiments are provided so that this disclosure will be thorough and complete, and will fully convey the scope of the present disclosure to those skilled in the art. A person with ordinary skill in the art to which the present disclosure pertains will understand that the inventive concept can be carried out under any appropriate condition.

In this specification, the terms are used only for explaining embodiments while not limiting the present disclosure. In this specification, the singular forms are intended to include the plural forms as well, unless the context clearly indicates otherwise. It will be understood that the terms 'comprises' and/or 'comprising', when used in this specification, specify the presence of stated components, steps, operations and/or elements, but do not exclude the presence or addition of one or more other components, steps, operations and/or elements.

In the specification, it will be understood that when a layer (or film) is referred to as being 'on' another layer or substrate, it can be directly on the other layer or substrate, or intervening layers may also be present.

It will be understood that, although the terms first, second, third, etc. may be used herein to describe various regions, films (or layers), these regions and films should not be limited by these terms. These terms are used only to distinguish a predetermined region or film (or layer) from another region or film (or layer). Therefore, a layer referred to as a first layer in one embodiment can be referred to as a second layer in another embodiment. Each embodiment described and exemplified herein includes a complementary embodiment thereof. Like reference numerals refer to like elements throughout.

Unless otherwise defined, all terms used in embodiments of the inventive concept have the same meaning as commonly understood by one of ordinary skill in the art to which the present disclosure belongs.

Hereinafter, a method for manufacturing a chemical sensor according to an embodiment of the inventive concept will be described with reference to the drawings. FIGS. 1 to 6 are perspective views to explain a method for manufacturing a chemical sensor according to an embodiment of the inventive concept.

Figure 1:
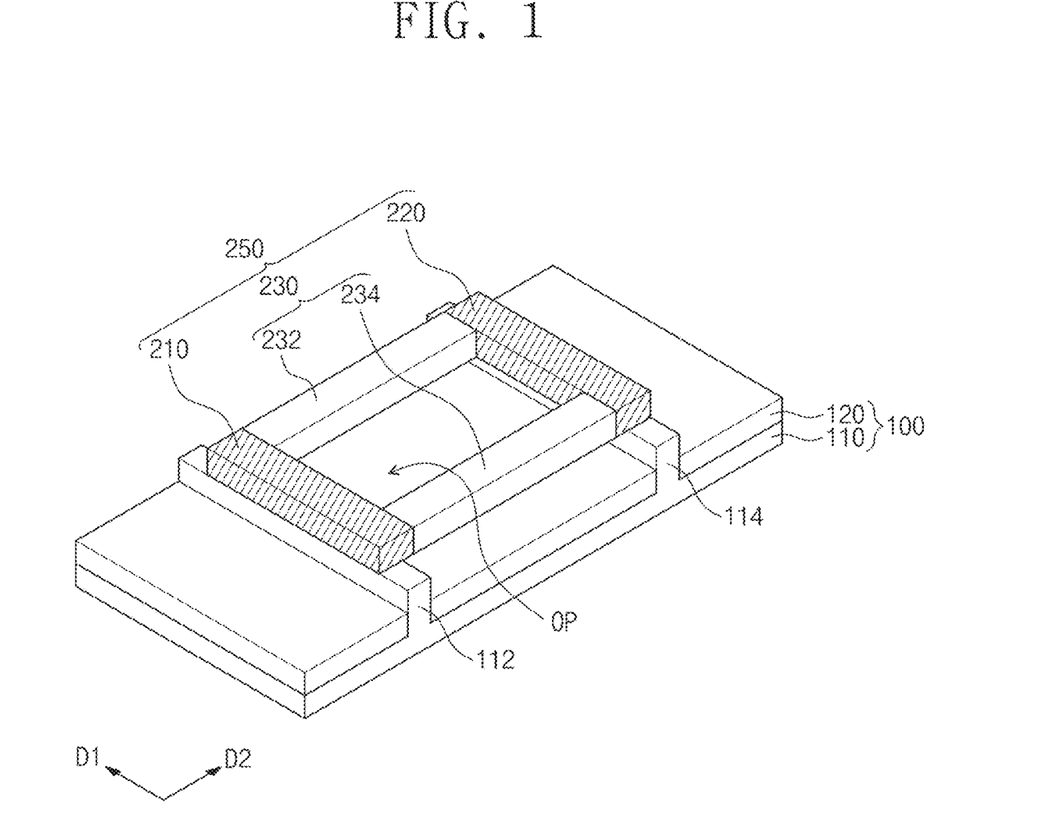
FIGS. 1 to 6 are perspective views to explain a method for manufacturing a chemical sensor according to an embodiment of the inventive concept.

Referring to FIG. 1, a dummy substrate 100 may be provided. The dummy substrate 100 may include a collector layer 110 and a dielectric layer 120 disposed on the collector layer 110. The collector layer 110 may include a first protrusion 112 and a second protrusion 114 that pass through the dielectric layer 120 and protrude from a top surface of the dielectric layer 120. The first protrusion 112 and the second protrusion 114 may extend in a first direction D1. The first protrusion 112 and the second protrusion 114 may be spaced apart from each other in a second direction D2 crossing the first direction D1. The collector layer 110 may include an electric conductor such as metal.

On the dummy substrate 100, an alignment frame 250 may be provided. The alignment frame 250 may have an opening OP that passes therethrough. For example, when viewed in a plane, the alignment frame 250 may have a rectangular ring shape. The alignment frame 250 may include a first side portion 210, a second side portion 220, and an insulation portion 230, which surround the opening OP. The first side portion 210 may be spaced apart from the second side portion 220 in the second direction D2. In this case, the first side portion 210 may be provided on the first protrusion 112, and the second side portion 220 may be provided on the second protrusion 114. Each of the first side portion 210 and the second side portion 220 may have a bar shape that extends in the first direction D1. The insulation portion 230 may connect both ends of the first side portion 210 and both ends of the second side portion 220, respectively. For example, the insulation portion 230 may include a first insulator 232 and a second insulator 234 which have bar shapes and extend in the second direction D2. The first insulator 232 may connect one end of the first side portion 210 and one end of the second side portion 220, and the second insulator 234 may connect the other end of the first side portion 210 and the other end of the second side portion 220. The insulation portion 230 may electrically connect the first side portion 210 and the second side portion 220. Each of the first side portion 210 and the second side portion 220 may be an electric conductor.

Figure 2:
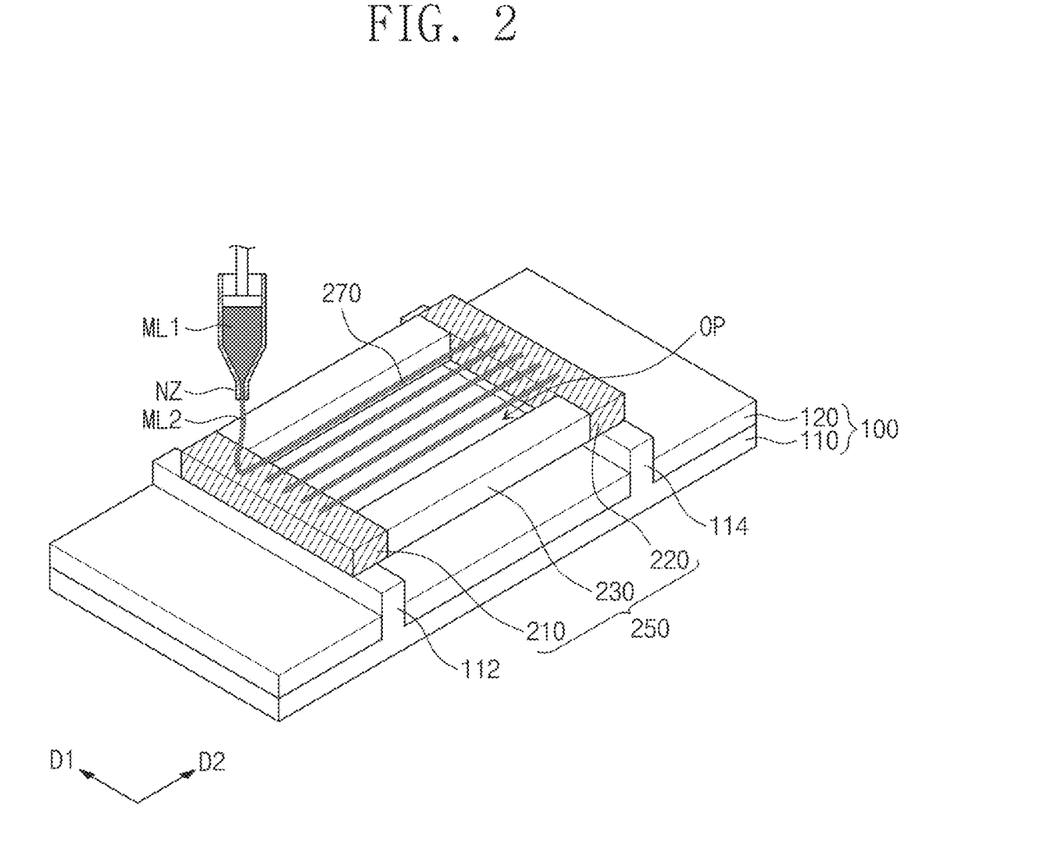

Referring to FIG. 2, a sensing fiber 270 may be provided on an alignment frame 250. The sensing fiber 270 may include an oxide semiconductor such as TiO2, or may include at least one of black phosphorus, or transition metal di-chalcogenide such as $MoSe_2$, $WSe_2$, $MoS_2$, $WS_2$, $SnS_2$, $TeS_2$, $MoTe_2$, or $WTe_2$. The sensing fiber 270 may be formed by an electro-spinning method. Hereinafter, a method for manufacturing the sensing fiber 270 will be described in detail.

A mixed solution ML1 for the electro-spinning may be manufactured. The mixed solution ML1 may include a solvent and a precursor material. For example, the solvent may include polyvinyl acetate (PVAc), poly vinyl alcohol (PVA), poly urethane (PU), polyimide (PI), polyethylene oxide (PEO), polyvinylpyrrolidone (PVP), polystyrene (PS), or polyacrylonitrile (PAN). The precursor material may include Ti tetraisopropoxide ($Ti(Oipr)_4$). Alternatively, the precursor material may include materials for providing a one-dimensional fiber structure that uses an oxide semiconductor, or the transition metal dichalcogenide such as $MoS_2$, $WS_2$, $SnS_2$, or $TeS_2$.

The sensing fiber 270 may be formed by ejecting the mixed solution ML1. For example, the mixed solution ML1 may be stored in a syringe of electro-spinning equipment, and then the mixed solution ML1 inside the syringe may be pushed out through a nozzle NZ. Through this, the mixed solution ML1 may be maintained at an end of the nozzle NZ in a form of liquid drop by a surface tension. The nozzle NZ and the collector layer 110 may be connected to an external power supply. A voltage may be applied in a vertical direction between the first side portion 210 and the nozzle NZ, and between the second side portion 220 and the nozzle NZ. When an electric filed applied from the outside becomes greater than the surface tension of the liquid drop, a finely conductive fiber pattern (ML2) may be provided from the nozzle NZ, and may drop onto the alignment frame 250. During the ejection of the conductive fiber pattern ML2, the nozzle NZ may move from the second side portion 220 toward the first side portion 210. Through this, the conductive fiber pattern ML2 may be ejected across the space between the first side portion 210 and the second side portion 220. The conductive fiber pattern ML2 is discharged from the end of the nozzle NZ, and then may be attached to the first side portion 210 and the second side portion 220 due to electrostatic repulsion against the voltage applied to the nozzle NZ.

Then, heat treatment may be performed on the conductive fiber pattern ML2. Through the heat treatment, the solvent contained in the conductive fiber pattern ML2 may be removed.

Through the above-described method, the sensing fiber 270 may be formed, extending from the top surface of the first side portion 210 to the top surface of the second side portion 220. However, the embodiment of the inventive concept is not limited. The electro-spinning method is one example of methods for forming the sensing fiber 270, and the sensing fiber 270 may be formed by various methods.

According to other embodiments of the inventive concept, metal oxide particles may be disposed on an outer surface of the sensing fiber 270. For example, a metal oxide catalyst may be added to the mixed solution ML1. The metal oxide catalyst may include Pt elements, Pd elements, or Au elements. The metal oxide catalyst may be bonded, in a form of particles, to the outer surface of the sensing fiber 270 during the ejection of the mixed solution ML1. When the metal oxide particles are provided on the outer surface of the sensing fiber 270, the resistance of the sensing fiber 270 may be reduced, and the sensing intensity of the chemical sensor may be increased.

Figure 3:
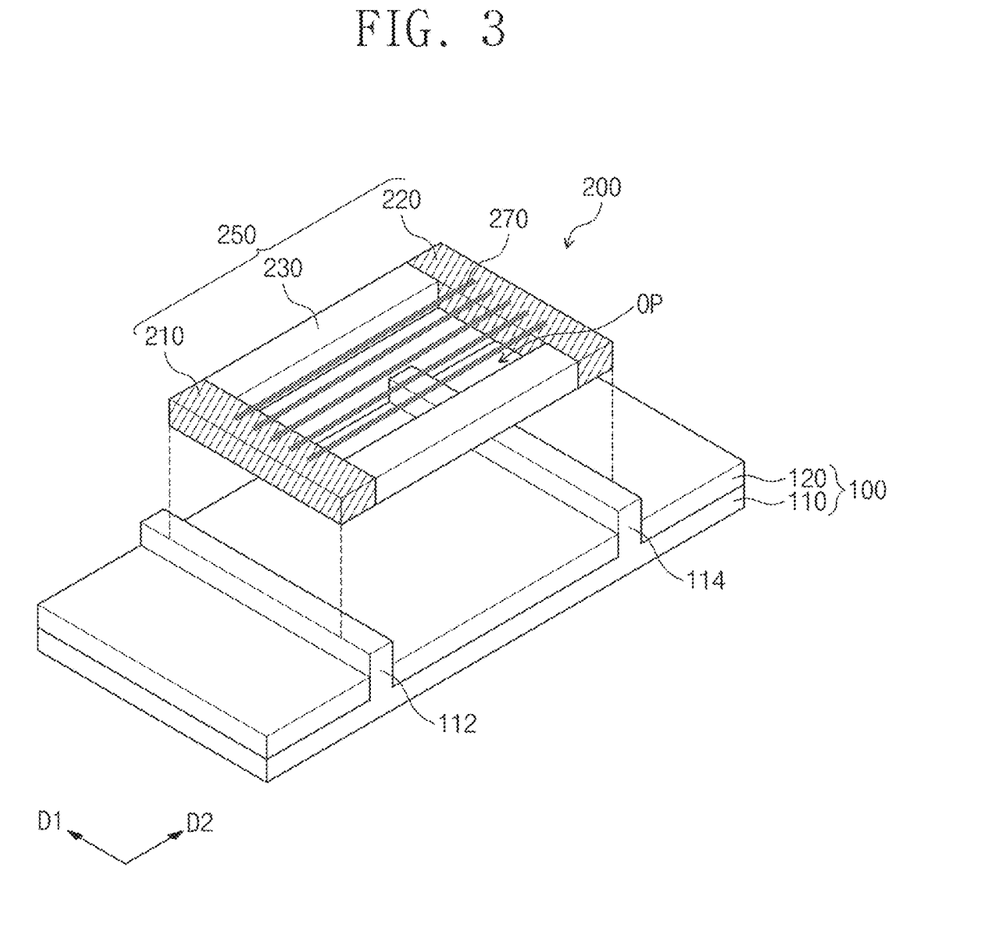

Referring to FIG. 3, an alignment frame 250 is separated from a dummy substrate 100, and thus a sensor part 200 may be manufactured. The dummy substrate 100 is reused, and then may be used in a process for manufacturing another sensor part 200.

Figure 4:
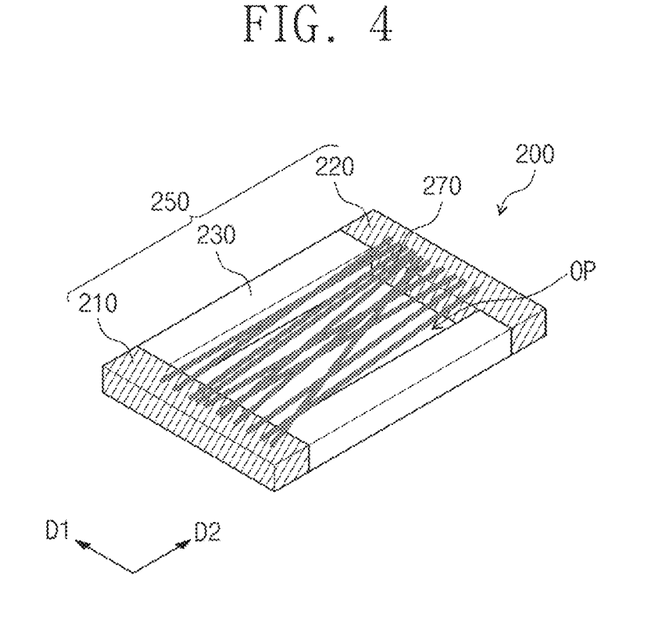

Referring to FIG. 4, a sensor part 200 may include an alignment frame 250 and a sensing fiber 270. The alignment frame 250 may include a first side portion 210, a second side portion 220, and an insulation portion 230, which surround an opening OP. The first side portion 210 may be spaced apart from the second side portion 220 in a second direction D2. The sensing fiber 270 may be disposed in two-dimensions between the first side portion 210 and the second side portion 220. For one example, the sensing fiber 270 passes through the opening OP of the alignment frame 250, and may connect the first side portion 210 and the second side portion 220. In detail, the sensing fiber 270 may be in a linear shape that extends from a top surface of the first side portion 210 to a top surface of the second side portion 220. The sensing fiber 270 may be provided in plurality. The sensing fiber 270 may be provided as separated individual fibers. As illustrated in FIG. 3, the sensing fibers 270 may be aligned in one direction (in this case, the second direction D2). Alternatively, as illustrated in FIG. 4, the sensing fibers 270 may be not aligned in one direction, but cross each other. According to another embodiment, the sensing fiber 270 may be provided in a form of fabric. For example, the plurality of sensing fibers 270 may extend in directions different from each other and overlap each other, on a surface parallel to the top surface of the first side portion 210 and the top surface of the second side portion 220. The sensing fiber 270 may electrically connect the first side portion 210 and the second side portion 220. When a target material is contacted to a surface of the sensing fiber 270, the sensing fiber 270 may change in electrical characteristics thereof.

Figure 5:
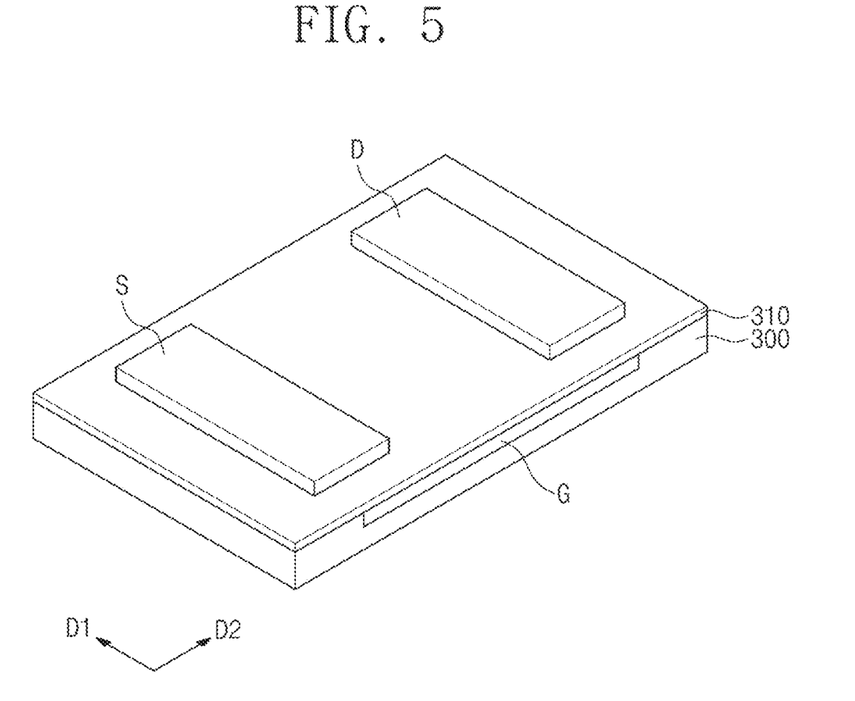

Referring to FIG. 5, a substrate 300 may be provided. The substrate 300 may include a gate pattern G buried therein, and a source pattern S and a drain pattern D which are disposed on a top surface thereof. The gate pattern G, the source pattern S, and the drain pattern D may extend in a first direction D1. The source pattern S and the drain pattern D may be spaced apart from each other in a second direction D2. The gate pattern G, the source pattern S, and the drain pattern D may be insulated from each other. For example, an insulation layer 310 may be disposed between the gate pattern G and the source pattern S, and between the gate pattern G and the drain pattern D.

Figure 6:
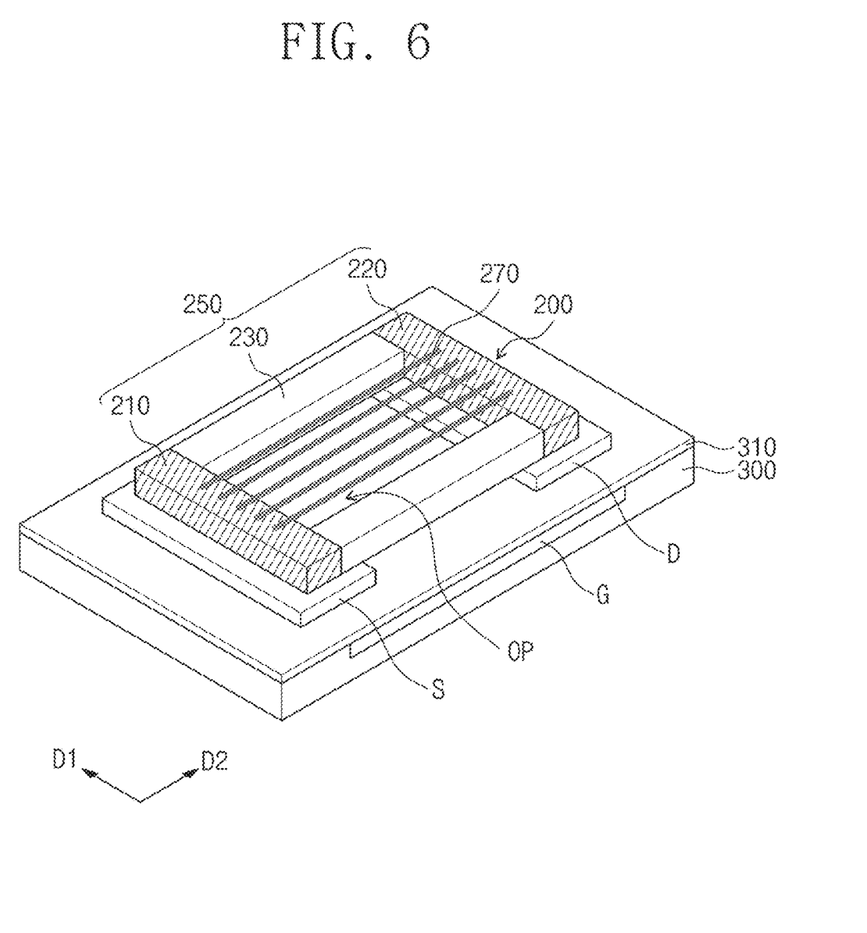

Referring to FIG. 6, a sensor part 200 may be transferred to a substrate 300. In this case, a first side portion 210 may be connected to a source pattern S, and a second side portion 220 may be connected to a drain pattern D. The sensor part 200 may be bonded to the substrate 300 through conductive adhesive such as silver paste. For example, the conductive adhesive is applied on the source pattern S and the drain pattern D, and then the first side portion 210 and the second side portion 220 may be disposed to contact the source pattern S and the drain pattern D, respectively. A sensing fiber 270 may be spaced apart from the substrate 300. That is, the sensing fiber 270 is supported by the first side portion 210 and the second side portion 220, and may float above the substrate 300. Accordingly, the sensing fiber 270, which floats above the substrate 300 between the first side portion 210 and the second side portion 220, may have a portion of which an entire outer surface is exposed to air. That is, the sensing fiber 270 may have a large area that may be contacted to a target material in air, which may increase the sensing sensitivity of the sensing fiber 270.

In a method for manufacturing a chemical sensor according to embodiments of the inventive concept, a sensor part 200 is separately made and then is transferred onto a substrate, and through this, the chemical sensor may be manufactured. The sensor part 200 to be separately provided may be applied to various parts according to the need, which may enhance the process efficiency. Also, for the sensor part 200, the mixed solution ML1 is electro-spun on an alignment frame 250, and thus the sensing fiber 270 may be formed, which may simplify a process for manufacturing the chemical sensor.

According to embodiments of the inventive concept, a chemical sensor may include a plurality of sensor parts.

Figure 7:
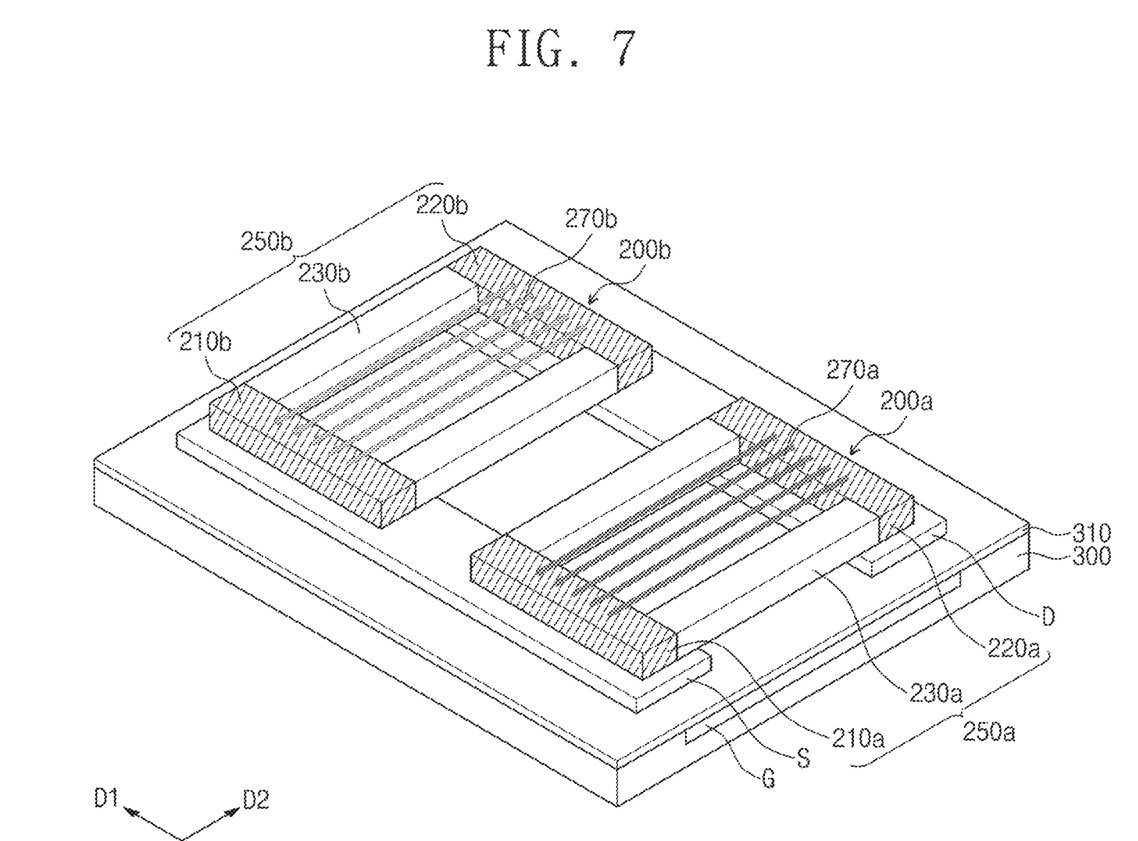
FIGS. 7 to 9 are perspective views to explain a chemical sensor according to embodiments of the inventive concept.
Figure 8:
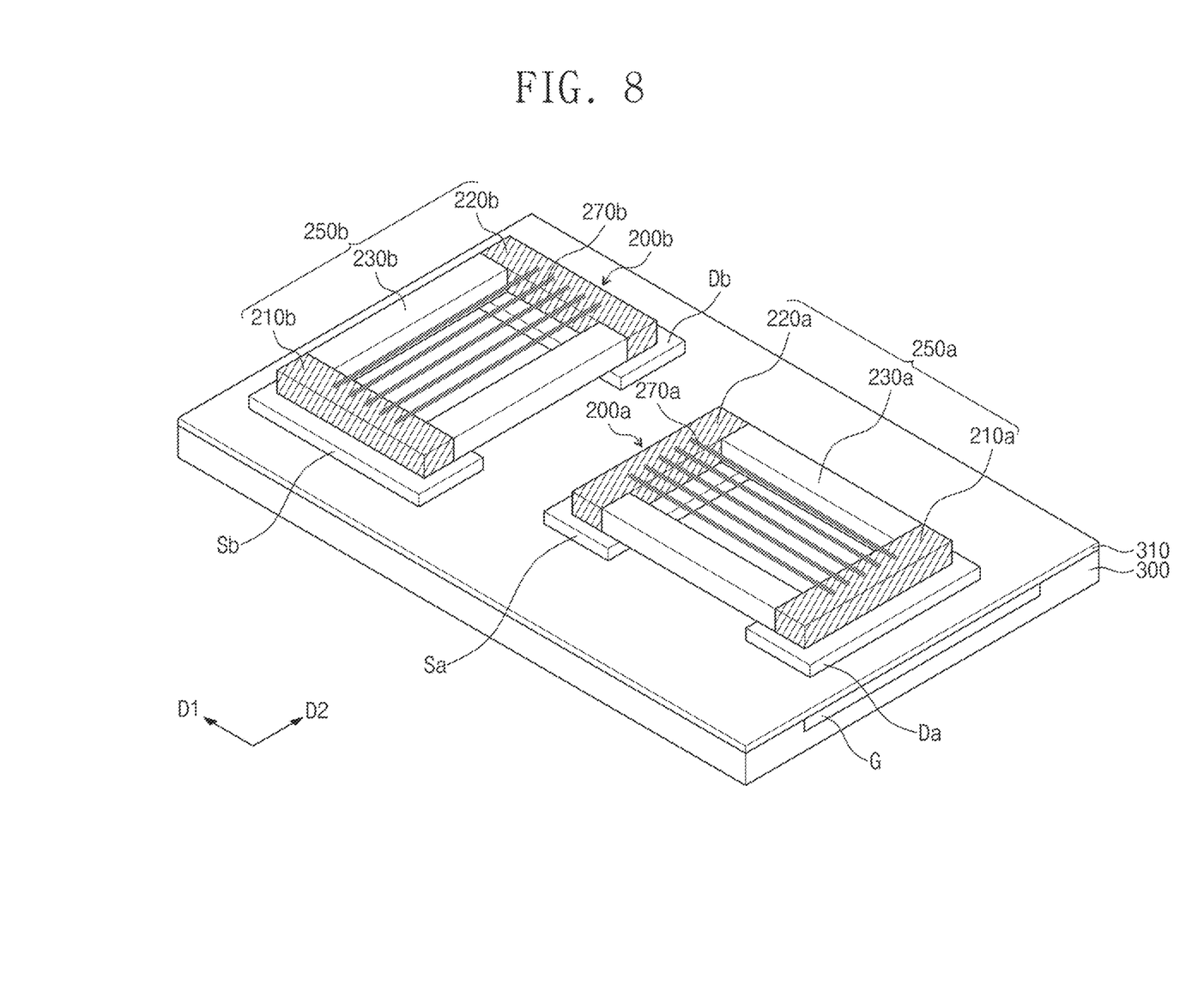
Figure 9:
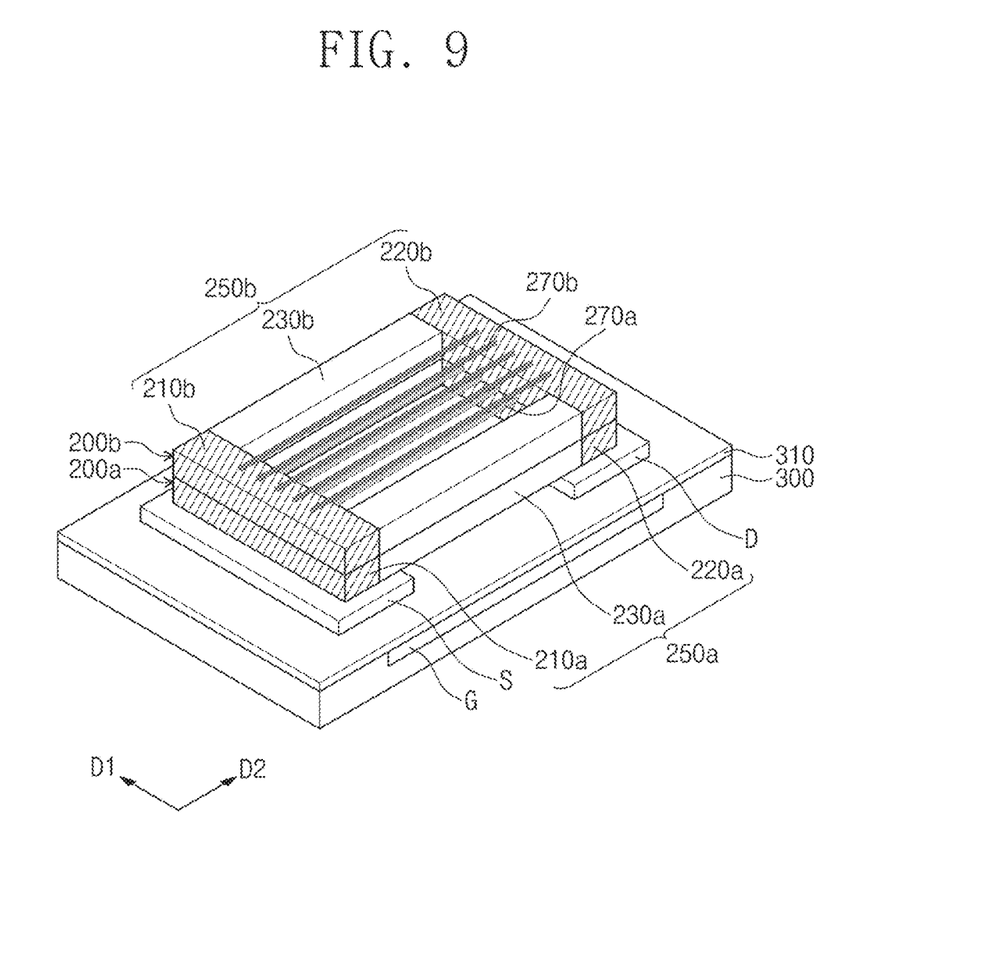

FIGS. 7 to 9 are perspective views to explain a chemical sensor according to embodiments of the inventive concept. About the components having the same reference numerals as those in FIGS. 1 to 4, their detailed descriptions will be omitted, or they will be simply explained for convenience of description.

As illustrated in FIG. 7, a chemical sensor may include a plurality of sensor parts that are transversely arranged.

A substrate 300 may include a gate pattern G buried therein, and a source pattern S and a drain pattern D which are disposed on a top surface thereof. The gate pattern G, the source pattern S, and the drain pattern D may extend in a first direction D1. The source pattern S and the drain pattern D may be spaced apart from each other in a second direction D2.

On the substrate 300, a first sensor part 200a may be provided. The first sensor part 200a may have an alignment frame 250a and a sensing fiber 270a. The first sensor part 200a may be manufactured through the manufacturing process of the sensor part, which is explained whit reference to FIGS. 1 to 3. The first sensor part 200a may have a first side portion 210a connected to the source pattern S of the substrate 300. The first sensor part 200a may have a second side portion 220a connected to the drain pattern D of the substrate 300.

On the substrate 300, a second sensor part 200b may be provided. The second sensor part 200b may have an alignment frame 250b and a sensing fiber 270b. The second sensor part 200b may be formed through substantially the same manufacturing process (for example, the manufacturing process of the sensor part explained with reference to FIGS. 1 to 3) as the first sensor part 200a. The alignment frame 250b of the second sensor part 200b may be substantially the same as the alignment frame 250a of the first sensor part 200a. The second sensor part 200b may have a first side portion 210b connected to the source pattern S of the substrate 300. The second sensor part 200b may have a second side portion 220b connected to the drain pattern D of the substrate 300. The sensing fiber 270b of the second sensor part 200b may have a material different from that of the sensing fiber 270a of the first sensor part 200a. The sensing fiber 270a of the first sensor part 200a may detect a target material different from that of the sensing fiber 270b of the second sensor part 200b.

Referring to FIG. 7, the first sensor part 200a and the second sensor part 200b, which are arranged in the same direction on one source pattern S and one drain pattern D, are described, but an embodiment of the inventive concept is not limited thereto.

As illustrated in FIG. 8, each of a first sensor part 200a and a second sensor part 200b may be disposed on different source and drain patterns S and D, and the first sensor part 200a and the second sensor part 200b may have different positions and arrangements that are different from each other. For example, a source pattern Sa and a drain pattern Da of the first sensor part 200a may extend in a second direction D2, and a sensing fiber 270a may extend in a first direction D1. A source pattern Sb and a drain pattern Db of the second sensor part 200b may extend in the first direction D1, and a sensing fiber 270b may extend in the second direction D2. However, the position and arrangement of each of the first sensor part 200a and the second sensor part 200b is not limited thereto.

As illustrated in FIG. 9, a chemical sensor may include a plurality of sensor parts that are vertically stacked.

A substrate 300 may include a gate pattern G buried therein, and a source pattern S and a drain pattern D which are disposed on a top surface thereof. The gate pattern G, the source pattern S, and the drain pattern D may extend in a first direction D1. The source pattern S, and the drain pattern D may be spaced apart from each other in a second direction D2.

On the substrate 300, a first sensor part 200a may be provided. The first sensor part 200a may have an alignment frame 250a and a sensing fiber 270a. The first sensor part 200a may have a first side portion 210a connected to the source pattern S of the substrate 300. The first sensor part 200a may have a second side portion 220a connected to the drain pattern D of the substrate 300.

On the sensor part 200a, a second sensor part 200b may be provided. The second sensor part 200b may include an alignment frame 250b and a sensing fiber 270b. The alignment frame 250b of the second sensor part 200b may be substantially the same as the alignment frame 250a of the first sensor part 200a. The second sensor part 200b may have a first side portion 210b connected to the first side portion 210a of the first sensor part 200a. The second sensor part 200b may have a second side portion 220b connected to the second side portion 220a of the first sensor part 200a. Accordingly, the first side portion 210b and the second side portion 220b of the second sensor part 200b may be electrically connected to the source pattern S and the drain pattern D of the substrate 300, through the first side portion 210a and the second side portion 220a of the first sensor part 200a, respectively. The sensing fiber 270b of the second sensor part 200b may have a material different from that of the sensing fiber 270a of the first sensor part 200a. The sensing fiber 270a of the first sensor part 200a may detect a target material different from that of the sensing fiber 270b of the second sensor part 200b.

The sensor parts of the chemical sensor according to embodiments of the inventive concept may be manufactured through independent processes, and the chemical sensor may detect a plurality of target materials through a configuration of disposing the sensor parts 200a and 200b that are separately formed on the substrate 300. Also, in the case where the sensor parts 200a and 200b are vertically stacked, a chemical sensor having a small area may be manufactured.

In the embodiments described with reference to FIGS. 7 to 9, the chemical sensor having two sensor parts is described, however the embodiments of the inventive concept is not limited thereto, and the chemical sensor may include three sensor parts or more.

The sensing fiber of the chemical sensor according to the embodiments of the inventive concept may have the large area that may be contacted to the target material in air, which may increase the sensing sensitivity of the chemical sensor.

In the method for manufacturing the chemical sensor according to the embodiments of the inventive concept, the sensor part may be formed through the separate process, and the sensor part may be applied to various parts according to the need, which may enhance the process efficiency. Also, the manufacturing process of the chemical sensor may be simplified.

The chemical sensor according to the embodiments of the inventive concept may detect the plurality of target materials through the configuration of disposing the sensor parts that are separately formed on the substrate. Also, in the case where the sensor parts are vertically stacked, the chemical sensor with the small area may be manufactured.

Although the embodiments of the inventive concept are described with reference to the accompanying drawings, those with ordinary skill in the technical field to which the inventive concept pertains will understand that the present disclosure can be carried out in other specific forms without changing the technical idea or essential features. Thus, the above-described embodiments are to be considered illustrative and not restrictive to all aspects.

What is claimed is:
1. A chemical sensor comprising:
an alignment frame having an opening that passes through the inside of the alignment frame, the alignment frame comprising first and second side portions that face each other with the opening therebetween and insulation portions disposed between the first and second side portions;

a plurality of sensing fibers disposed in two-dimensions across the opening of the alignment frame so as to connect the first side portion and the second side portion; and a source pattern and a drain pattern connected to the first side portion and the second side portion of the alignment frame, respectively.

2. The chemical sensor of claim 1, wherein the sensing fibers extend from a top surface of the first side portion to a top surface of the second side portion.

3. The chemical sensor of claim 1, wherein both ends of the first side portion are connected to both ends of the second side portion through the insulation portions of the alignment frame, respectively.

4. The chemical sensor of claim 3, wherein the alignment frame has a plane with a rectangular ring shape.

5. The chemical sensor of claim 1, wherein each of the first side portion and the second side portion is an electric conductor.

6. The chemical sensor of claim 1, wherein the sensing fibers comprise at least one of $MoSe_2$, $WSe_2$, $MoS_2$, $WS_2$, $SnS_2$, $TeS_2$, $MoTe_2$, $WTe_2$, or black phosphorus.

7. The chemical sensor of claim 1, further comprising metal oxide particles disposed on outer surfaces of the sensing fibers.

8. A chemical sensor comprising:
a plurality of sensor parts; and
a substrate comprising a source pattern and a drain pattern that are electrically connected to the sensor parts,
wherein each of the sensor parts comprises:
a first side portion that is conductive, and connected to the source pattern;
a second side portion that is conductive, and connected to the drain pattern and spaced apart from the first side portion;
insulation portions that connect both ends of the first side portion and both ends of the second side portion, respectively; and
a sensing fiber that is disposed between the insulation portions to connect the first side portion and the second side portion,
wherein a sensing fiber in one of the sensor parts detects a target material different from that of a sensing fiber in another one of the sensor parts.

9. The chemical sensor of claim 8, wherein each of the source pattern and the drain pattern extends in a first direction, and
the sensor parts are horizontally spaced apart from each other in the first direction.

10. The chemical sensor of claim 8, wherein the sensor parts are stacked vertically,
a first side portion in one of the sensor parts overlaps and contacts a first side portion of a sensing fiber in another one of the sensor parts, and
a second side portion in one of the sensor parts overlaps and contacts a second side portion of a sensing fiber in another one of the sensor parts.

11. A method for manufacturing a chemical sensor, comprising:
forming a sensor part; and
transferring the sensor part onto a substrate so as to be connected to a source pattern and a drain pattern of the substrate,
wherein the forming of the sensor part comprises:
providing an alignment frame, which has an opening, on a dummy substrate;
forming a sensing fiber across the opening of the alignment frame; and
separating the alignment frame from the dummy substrate.

12. The method of claim 11, wherein the alignment frame comprises:
first and second side portions that face each other with the opening therebetween and are insulated from each other; and
insulation portions that connect both ends of the first side portion and both ends of the second side portion, respectively,
wherein the sensing fiber connects the first side portion and the second side portion.

13. The method of claim 11, wherein the sensing fiber is formed through an electro-spinning method.

* * * * *